(12) United States Patent
Hiller

(10) Patent No.: US 11,230,383 B2
(45) Date of Patent: Jan. 25, 2022

(54) AIRCRAFT AIR DUCT SYSTEM FOR TRANSMITTING ELECTRICAL POWER AND VISIBLE LIGHT

(71) Applicant: The Boeing Company, Chicago, IL (US)

(72) Inventor: Nathan D Hiller, Irvine, CA (US)

(73) Assignee: The Boeing Company, Chicago, IL (US)

( * ) Notice: Subject to any disclaimer, the term of this patent is extended or adjusted under 35 U.S.C. 154(b) by 105 days.

(21) Appl. No.: 16/782,473

(22) Filed: Feb. 5, 2020

(65) Prior Publication Data

US 2021/0237883 A1 Aug. 5, 2021

(51) Int. Cl.
| | | |
|---|---|---|
| B64D 13/06 | (2006.01) | |
| B64D 47/02 | (2006.01) | |
| B60Q 3/41 | (2017.01) | |
| H01L 35/30 | (2006.01) | |
| F21V 7/00 | (2006.01) | |
| F21V 9/06 | (2018.01) | |
| A61L 9/20 | (2006.01) | |
| F21Y 115/10 | (2016.01) | |
| F21W 106/00 | (2018.01) | |
| F21W 107/30 | (2018.01) | |

(52) U.S. Cl.
CPC .............. *B64D 13/06* (2013.01); *A61L 9/20* (2013.01); *B60Q 3/41* (2017.02); *B64D 47/02* (2013.01); *F21V 7/0008* (2013.01); *F21V 9/06* (2013.01); *H01L 35/30* (2013.01); *A61L 2209/12* (2013.01); *B64D 2013/0644* (2013.01); *B64D 2203/00* (2013.01); *B64D 2211/00* (2013.01); *F21W 2106/00* (2018.01); *F21W 2107/30* (2018.01); *F21Y 2115/10* (2016.08)

(58) Field of Classification Search
CPC ... A61L 9/20; A61L 2209/12; B60Q 3/41–44; B64D 13/06; B64D 47/02; B64D 2013/0644; B64D 2203/00; B64D 2211/00; F21V 7/0008; F21V 9/06; F21W 2106/00; F21W 2107/30; F21Y 2115/10; H01L 35/30
See application file for complete search history.

(56) References Cited

U.S. PATENT DOCUMENTS 9,205,287 B2 * 12/2015 Castanha ............... B64D 11/00

* cited by examiner

*Primary Examiner* — Jason M Han
(74) *Attorney, Agent, or Firm* — Vivacqua Crane PLLC

(57) ABSTRACT

An air duct system comprising an air duct having a main body, a visible light source, and one or more photovoltaic devices. The main body of the air duct defines a passageway having a reflective inner surface. The visible light source is configured to generate visible light, where the visible light source directs the visible light along the reflective inner surface of the air duct. The one or more photovoltaic devices are disposed along the reflective inner surface of the air duct, where a portion of the visible light generated by the visible light source is converted into electrical power by the one or more photovoltaic devices.

21 Claims, 11 Drawing Sheets

Forced Convection

Natural Convection

Conduction

US 11,230,383 B2

AIRCRAFT AIR DUCT SYSTEM FOR TRANSMITTING ELECTRICAL POWER AND VISIBLE LIGHT

INTRODUCTION

The present disclosure relates to an air duct system. More particularly, the present disclosure is directed towards an air duct system configured to transmit air, visible light, and electrical power.

BACKGROUND

There is an ongoing effort to reduce the weight of an aircraft. A reduction in weight typically results in a corresponding reduction in fuel consumption of the aircraft and may also allow for an increase in payload capacity. Electrical power, current, and electronic signals are typically conducted through wires or cables constructed of copper or aluminum as the conductive medium. For example, wiring is used in the passenger cabin of the aircraft to power various electronic devices such as, for example, overheard lighting and displays. However, wiring contributes significantly to the total weight of the aircraft.

SUMMARY

According to several aspects, an air duct system is disclosed. The air duct system includes an air duct having a main body, where the main body of the air duct defines a passageway having a reflective inner surface. The air duct system also includes a visible light source configured to generate visible light. The visible light source directs the visible light along the reflective inner surface of the air duct. The air duct system also includes one or more photovoltaic devices disposed along the reflective inner surface of the air duct, where a portion of the visible light generated by the visible light source is converted into electrical power by the one or more photovoltaic devices.

In another aspect, an air duct system is disclosed. The air duct system includes an air duct having a main body, where the main body of the air duct defines a passageway having a reflective inner surface. The air duct system also includes a visible light source configured to generate visible light, where the visible light source directs the visible light along the reflective inner surface of the air duct. The air duct system further includes an emitter configured to emit radio frequency waves, where the emitter directs the radio frequency waves along the reflective inner surface of the air duct. Finally, the air duct system includes one or more antennas that are each connected to a corresponding power harvesting circuit, where the radio frequency waves are received by the one or more antennas and are converted into electrical power by the corresponding power harvesting circuit.

In still another aspect, a method for transmitting air, visible light, and electrical power through an air duct of an aircraft is disclosed. The method includes receiving, by the air duct, conditioned air and visible light. The method also includes directing the visible light along a reflective inner surface of the air duct, where the visible light reflects off of the reflective inner surface and travels along a passageway of the air duct. Finally, the method includes converting a portion of the visible light into electrical power by one or more photovoltaic devices disposed along the reflective inner surface of the air duct.

In another aspect, an air duct system is disclosed. The air duct system includes an air duct having a main body, where the main body of the air duct defines a passageway and an outer surface. The air duct system also includes one or more thermoelectric generators, where each thermoelectric generator includes a hot side and a cold side, and the hot side of the thermoelectric generator is positioned along the outer surface of the air duct.

The features, functions, and advantages that have been discussed may be achieved independently in various embodiments or may be combined in other embodiments further details of which can be seen with reference to the following description and drawings.

BRIEF DESCRIPTION OF THE DRAWINGS

The drawings described herein are for illustration purposes only and are not intended to limit the scope of the present disclosure in any way.

DETAILED DESCRIPTION

The present disclosure is directed towards an air duct system configured to transmit air, visible light, and electrical power to passengers in a vehicle, such as an aircraft. The air duct system includes an air duct that defines a passageway having a reflective inner surface and a visible light source that directs visible light along the reflective inner surface of the air duct. The disclosed air duct system also includes one or more photovoltaic devices disposed along the reflective inner surface of the air duct. A portion of the visible light generated by the visible light source is converted into electrical power by the photovoltaic device. Accordingly, the disclosed air duct system transmits electrical power without utilizing wiring or cables. In an embodiment, the disclosed air duct system is used to transmit visible light to the overhead lights in an aircraft, and the electrical power from the photovoltaic devices is used to provide electrical power to an electronic device such as a television display. The disclosed air duct system does not require wiring to transmit electrical power to the overhead lighting and the television display in the interior cabin of an aircraft, and results in a significant reduction in weight.

In an embodiment, the disclosed air duct system includes an ultraviolet light source that emits ultraviolet light. The ultraviolet light is configured to sanitize the air flowing through the passageway of the air duct by killing airborne bacteria and other germs that are suspended within the air flowing through the air duct. In an embodiment, the ultraviolet light source is utilized in combination with the visible light source. Alternatively, in another embodiment, the ultraviolet light source is used alone.

In still another embodiment, the disclosed air duct system only transmits air. In other words, no visible light or ultraviolet light is transmitted through the air duct. Instead, the air duct includes one or more thermoelectric generators disposed along an outer surface of the air duct. The thermoelectric generator is configured to transform heat along the outer surface of the air duct into electrical energy that may be used by one or more systems in the aircraft.

The following description is merely exemplary in nature and is not intended to limit the present disclosure, application, or uses.

Figure 1:
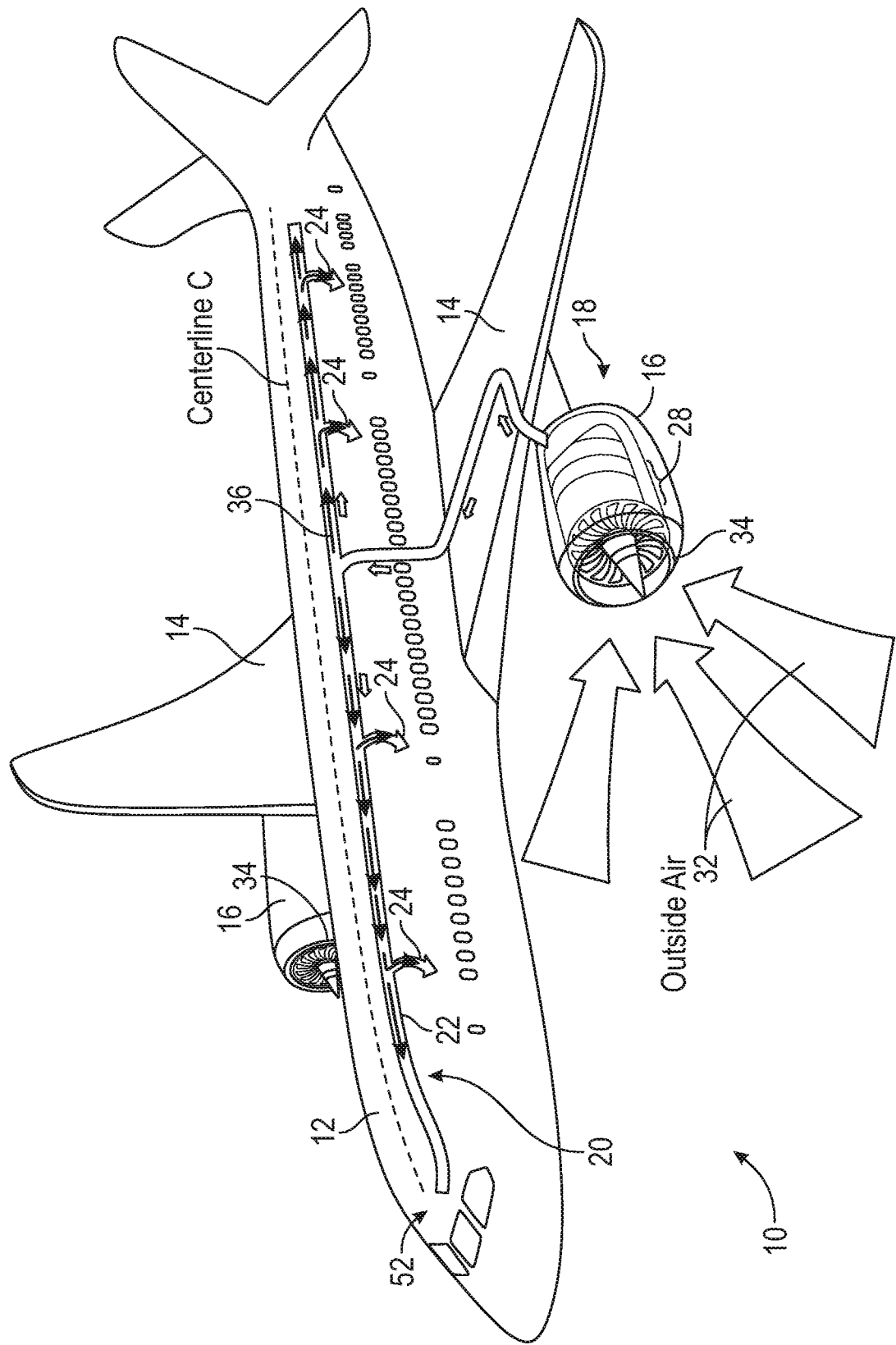
FIG. 1 is a perspective, partially sectioned view of an aircraft with the disclosed air duct system, according to an exemplary embodiment.

Referring to FIG. 1, a partially cross-sectioned aircraft 10 is shown. The aircraft 10 includes a fuselage 12, a pair of wings 14, a nacelle 16 mounted to each wing 14, a main engine 18 housed within each nacelle 16 (only one of the main engines 18 are shown), and an air duct system 20. The air duct system 20 includes an overhead air duct 22 and a plurality of distribution ducts 24. Outside air 32 enters the main engine 18 through an inlet 34 and is compressed and heated by a compressor section 28 of the main engine 18 into heated pressurized air. A portion of the heated pressurized air from the compressor sections 28 of the main engine 18, which is referred to as bleed air, is cooled and then remixed with recirculated air to create conditioned air 36. The conditioned air 36 is set to a predetermined temperature. The conditioned air 36 flows through the overhead air duct 22, to the distribution ducts 24, and is delivered throughout an interior cabin 58 (FIG. 2) of the aircraft 10.

In the non-limiting embodiment as shown in FIG. 1, the overhead air duct 22 is linear and extends along a centerline C of the aircraft 10. However, it is to be appreciated that the overhead air duct 22 may include a non-linear or curved profile as well. Moreover, although the figures illustrate the disclosed air duct system 20 as part of an aircraft, the air duct system 20 may be used in other applications as well.

Figure 2:
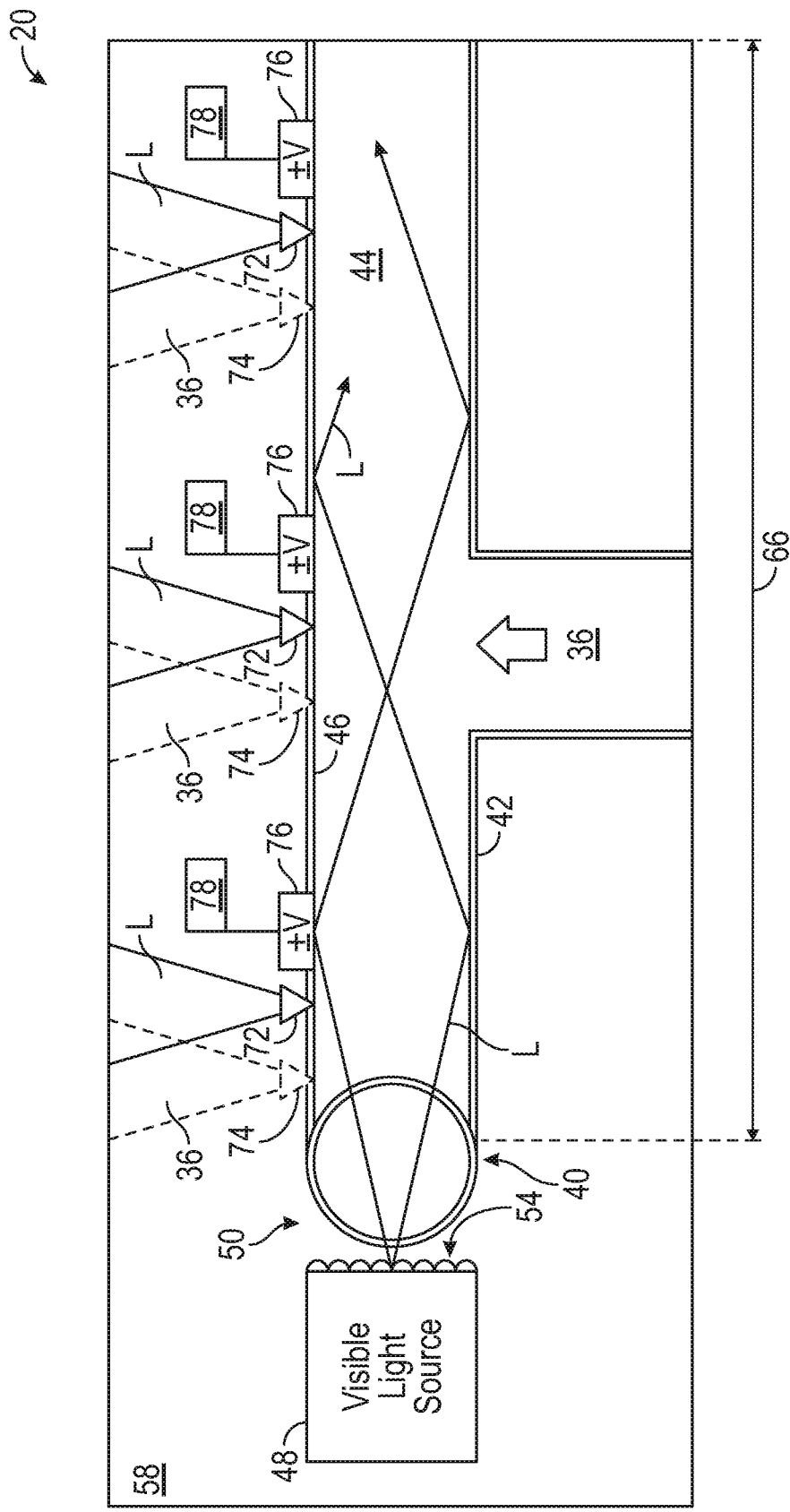
FIG. 2 is a schematic diagram of the air duct system including a visible light source and one or more photovoltaic devices configured to transform visible light into electrical power, according to an exemplary embodiment.

FIG. 2 is a schematic diagram of an embodiment of the air duct system 20 for transmitting visible light L and electrical energy. As explained below, the disclosed air duct system 20 is configured to transmit air, visible light, and electrical power. Specifically, a portion of the visible light L is transformed into electrical power. In another embodiment, the disclosed air duct system 20 includes an ultraviolet light source 30 (seen in FIG. 7) that exposes the conditioned air 36 flowing through the overhead air duct 22 to ultraviolet light. The ultraviolet light emitted by the ultraviolet light source 30 is of a frequency or intensity sufficient to sanitize air.

Turning back to FIG. 2, the air duct system 20 includes an air duct 40 having a main body 42. The main body 42 of the air duct 40 defines a passageway 44 having a reflective inner surface 46, where the conditioned air 36 and the visible light L are transmitted through the passageway 44. The reflective inner surface 46 of the main body 42 of the air duct 40 includes a reflectance of at least fifty percent. For example, an aluminum coating would provide a reflectance of at least fifty percent. However, in an embodiment the reflective inner surface 46 of the main body of the air duct 40 includes a reflectance of at least ninety-nine percent. One example of a material for coating the reflective inner surface 46 of the air duct 40 that has a reflectance of at least ninety-nine percent is a reflective film. In an embodiment, the reflective film is applied to the air duct 40 during fabrication. In an alternative embodiment, a conventional air duct system is retrofitted by applying the reflective film to the inner surface of the conventional air duct. One commercially available example of a reflective film is Specular Film DF2000MA, which is available from the 3M Company of Maplewood, Minn. In another embodiment, the reflective inner surface 46 is coated with an optical supermirror, a Bragg grating, photonic crystal, or a nanostructured materials. A Bragg grating is a reflecting structure having a periodic refractive index modulation.

The air duct system 20 also includes a visible light source 48 configured to generate the visible light L, where the visible light source 48 directs the visible light L along the reflective inner surface 46 of the air duct 40. The visible light L then impinges against the reflective inner surface 46 and travels along the passageway 44 of the air duct 40. In one embodiment, the visible light source 48 is positioned at an end 50 of the air duct 40 situated at the front end 52 of the aircraft 10 (FIG. 1). However, it is to be appreciated that the position of the visible light source 48 is not limited to this configuration as long as the visible light L is directed towards the reflective inner surface 46 of the air duct 40 and is transmitted along a length 66 of the air duct 40. In one non-limiting embodiment, the visible light source 48 includes an array of light-emitting diodes (LEDs) 54. In an embodiment, the LEDs 54 emit white light at ten kilowatts, however, it is to be appreciated that other types of devices that emit visible light may be used as well. Furthermore, it is also to be appreciated that the visible light L is not limited to only white light. Instead, the visible light L may be of any color and intensity that is required for a particular application.

Figure 3:
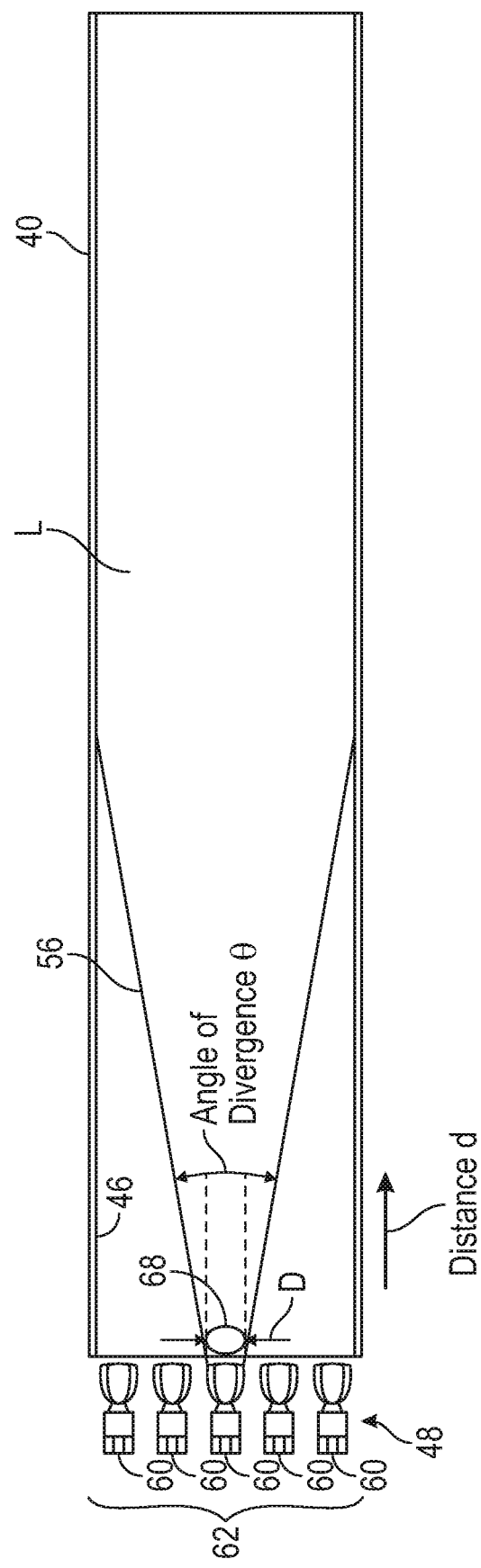
FIG. 3 is a schematic diagram of a single beam of visible light being transmitted by the visible light source, according to an exemplary embodiment.

FIG. 3 is an illustration of a light beam 56 emitted from a lamp 60. The lamp 60 is part of an array 62 of lamps 60 that are the visible light source 48. For purposes of clarity, only one of lamps 60 is emitting visible light L in FIG. 3. In an embodiment, the lamps 60 are parabolic aluminized reflector lamps, however, it is to be appreciated that other types of lamps may be used as well. The light beam 56 is semi-culminated, which means that the light beam 56 emitted from the visible light source 48 (i.e., the lamps 60) has an angle of divergence θ of ten degrees or less. The angle of divergence θ represents the amount of angular spread that the light beam 56 undergoes as the distance d from the visible light source 48 increases. As seen in FIG. 3, the light beam 56 diverges away from a center diameter D, where the center diameter D represents a maximum intensity 68 of the light beam 56. The light beam 56 is semi-culminated so as to direct the visible light L along the reflective inner surface 46 of the air duct 40.

Referring back to FIG. 2, the air duct system 20 further includes one or more of lighting apertures 72 disposed along the main body 42 of the air duct 40, where a portion of the visible light L generated by the visible light source 48 exits the air duct 40 through the lighting apertures 72. The lighting apertures 72 each represent the overhead light for a passenger located within the interior cabin 58 of the aircraft 10 (FIG. 1). Accordingly, the lighting apertures 72 replace a traditional lamp that is used to provide visible light to a passenger. The lighting apertures 72 also eliminate the need to route wiring or cables through the air duct 40 as well, which in turn reduces weight in the aircraft 10. The air duct 40 further includes one or more air valves 74 disposed along the main body 42 of the air duct 40. The air valves 74 are each configured to release the conditioned air 36 (FIG. 1) that travels through the air duct system 20.

Continuing to refer to FIG. 2, the air duct system 20 also includes one or more photovoltaic devices 76 that are disposed along the reflective inner surface 46 of the air duct 40. A portion of the visible light L generated by the visible light source 48 impinges against each photovoltaic device 76 and is then converted into electrical power by the photovoltaic devices 76. In the embodiment as shown, each photovoltaic device 76 provides electrical power to a corresponding electronic device 78. In an embodiment, an individual electronic device 78 is provided for each passenger in the aircraft 10. For example, in one embodiment, the electronic device 78 is a television display that is provided to each passenger seated within the interior cabin 58 of the aircraft 10. Some examples of photovoltaic devices 76 include, but are not limited to, crystalline silicon photovoltaic devices having an efficiency of about 25%, multi-junction photovoltaic devices having an efficiency of about 45%, and perovskite photovoltaic devices. Since the silicon photovoltaic devices produce less electrical power, they may be used in lower-cost application.

As seen in FIG. 2, a single lighting aperture 72, a single air valve 74, a single photovoltaic device 76, and a single electronic device 78 are provided for each passenger of the aircraft 10. However, in another embodiment, the power from multiple photovoltaic devices 76 are combined together to provide power to a single electronic device 78 requiring more electrical energy than a single electronic device allotted to a passenger, such as a television screen. For example, in another embodiment, the power generated from a plurality of the photovoltaic devices 76 are combined together to provide power to an electronic device such as a microwave.

Figure 4:
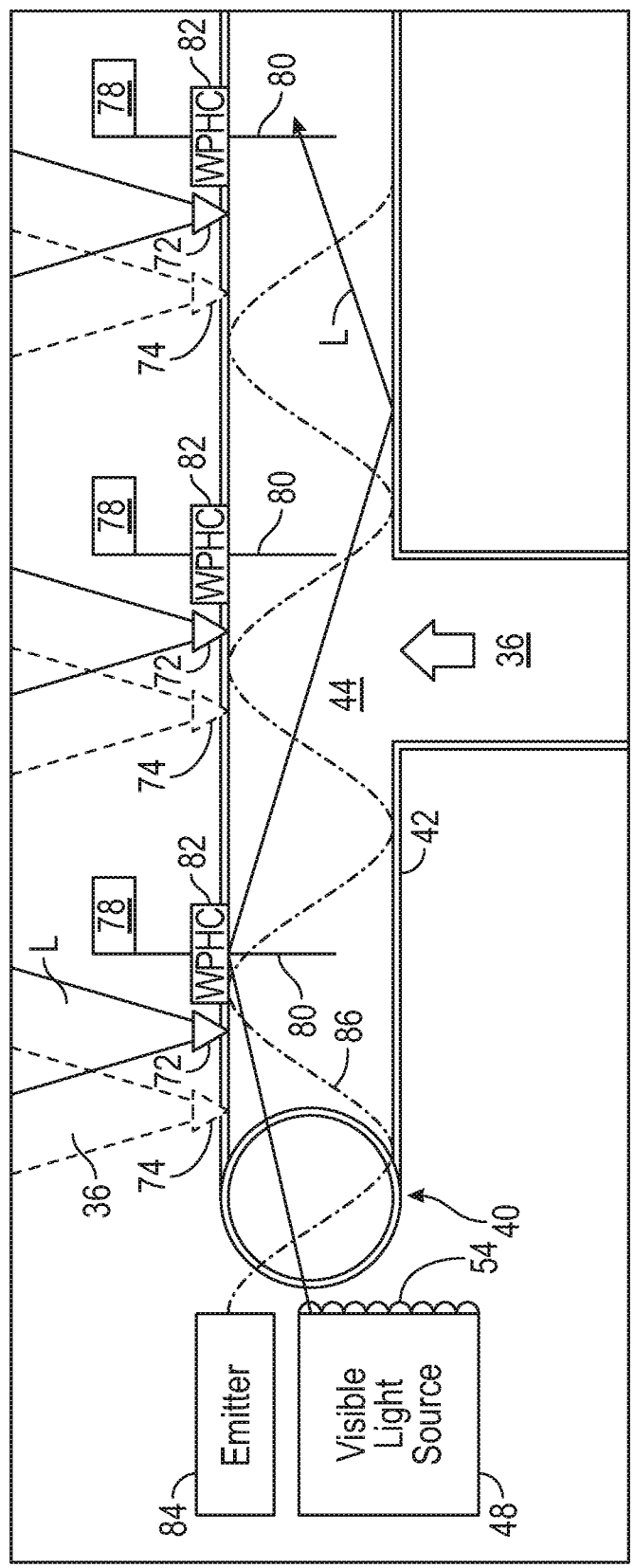
FIG. 4 is an alternative embodiment of the air duct system in FIG. 2 having a radio frequency emitter, one or more antennas, and one or more power harvesting circuits, according to an exemplary embodiment.

Although FIG. 2 illustrates photovoltaic devices 76 for transforming the visible light L into electrical energy, in one embodiment the photovoltaic devices 76 are omitted. Instead, as shown in FIG. 4, the photovoltaic devices 76 are replaced by an antenna 80 and a power harvesting circuit 82. In the embodiment as shown in FIG. 4, the air duct system 20 further includes an emitter 84 configured to emit radio frequency waves 86. The emitter 84 directs the radio frequency waves 86 along the reflective inner surface 46 of the air duct 40. The radio frequency waves 86 impinge against the reflective inner surface 46 of the air duct 40 and are intercepted by one of the antennas 80. It is to be appreciated that the reflective inner surface 46 of the air duct 40 reflects the radio frequency waves 86. Therefore, the radio frequency waves 86 travel through the air duct 40 and are not transmitted to other surrounding components of the aircraft 10. As seen in FIG. 4, the antennas 80 each extend partially into the passageway 44 of the air duct 40. Therefore, the antennas 80 are each positioned to intercept the radio frequency waves 86 that travel through the air duct 40.

Figure 5:
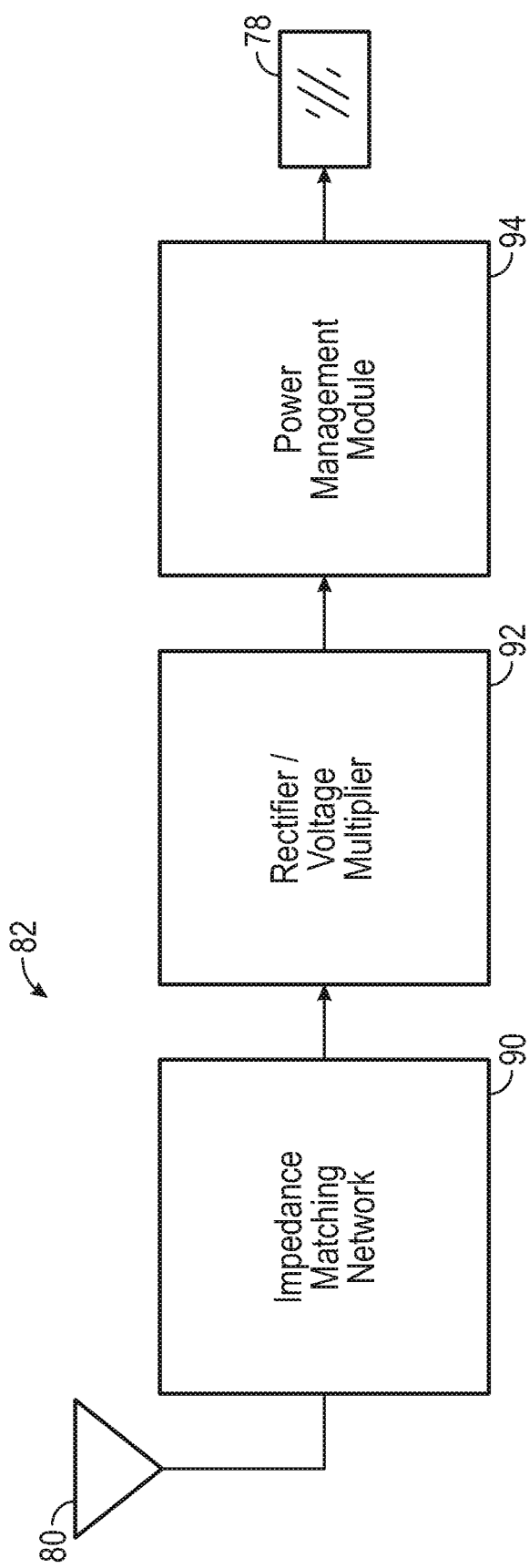
FIG. 5 is a schematic diagram of the power harvesting circuit shown in FIG. 4, according to an exemplary embodiment.

The antennas 80 are each connected to a corresponding power harvesting circuit 82, where the radio frequency waves 86 are received by the antennas 80 and are converted into electrical power by the corresponding power harvesting circuits 82. FIG. 5 is a schematic diagram illustrating an embodiment of the power harvesting circuit 82. In the embodiment as shown in FIG. 5, the power harvesting circuit 82 includes an impedance matching network 90, a combined rectifier and voltage multiplier 92, and a power management module 94. The impedance matching network 90 is configured to transform the impedance of the antenna 80 into a transmission impedance of the power harvesting circuit 82. The combined rectifier and voltage multiplier 92 is configured to convert the radio frequency waves 86 into DC power, which provides the voltage required by the electronic devices 78. The power management module 94 stores the electrical energy and provides the electrical energy to the corresponding electronic device 78. Turning back to FIG. 4, it is to be appreciated that since the visible light source 48 is not used to transmit electrical energy, the visible light L may be less intense when compared to a visible light source 48 for transmitting both electrical power and visible light.

FIGS. 6A-6D illustrate yet another embodiment of the air duct system 20 including one or more thermoelectric generators 100 disposed along an outer surface 102 of the air duct 40. It is to be appreciated that heat is generated as the visible light L impinges against the reflective inner surface 46 of the air duct 40. Heat is also produced when the radio frequency waves 86 (seen in FIG. 4) or the ultraviolet light U (seen in FIG. 7) impinges against the reflective inner surface 46 of the air duct 40 as well. The thermoelectric generator 100 is configured to transform the heat into electrical energy that may be used by one or more systems in the aircraft 10. The thermoelectric generator 100 is a thermoelectric module, such as a solid state thermoelectric module.

Figure 6B:
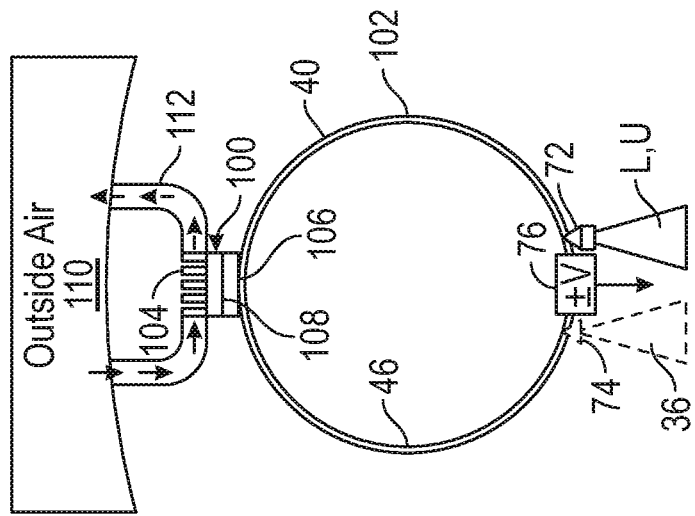
FIG. 6B illustrates the thermoelectric generator in FIG. 6A cooled by forced convection, according to an exemplary embodiment.
Figure 6A:
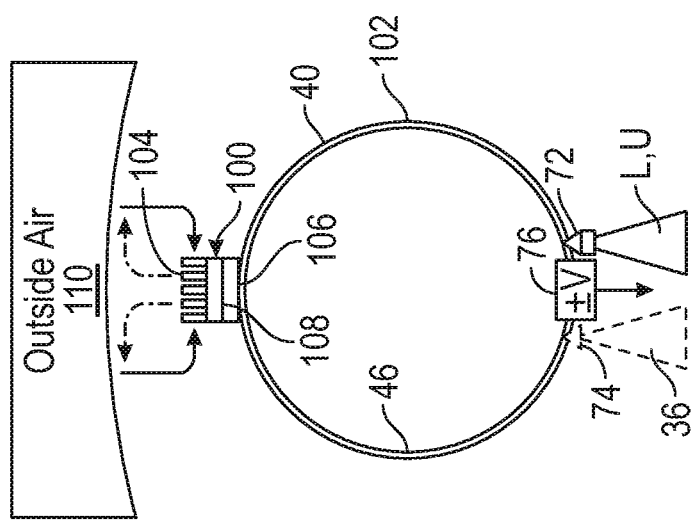
FIG. 6A illustrates a thermoelectric generator disposed along an outer surface of the air duct, where the thermoelectrical generator cooled by natural convection, according to an exemplary embodiment.
Figure 6D:
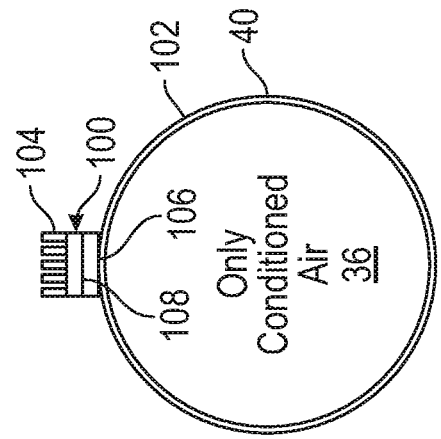
FIG. 6D illustrates the thermoelectric generator disposed along another embodiment of the air duct only transmitting the conditioned air, according to an exemplary embodiment.
Figure 6C:
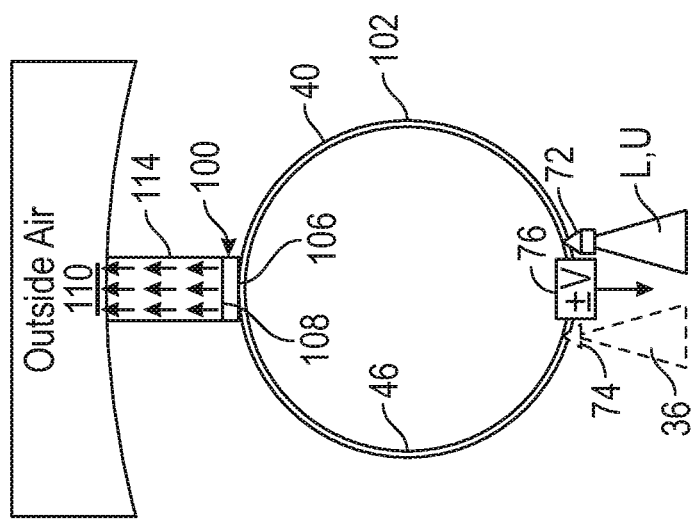
FIG. 6C illustrates the thermoelectric generator cooled by conduction, according to an exemplary embodiment.

The thermoelectric generator 100 includes a heat sink 104 (in the embodiment as shown in FIG. 6C, the heat sink 104 is omitted). The thermoelectric generator 100 also includes a hot side 106 and a cold side 108. The hot side 106 of the thermoelectric generator 100 is positioned along the outer surface 102 of the air duct 40. In an embodiment, the thermoelectric generator 100 is physically attached to outer surface 102 of the air duct 40 by adhesives or mechanical attachments such as screws or brackets (not shown). The cold side 108 of the thermoelectric generator 100 opposes the hot side 106 of the thermoelectric generator 100 and contacts the heat sink 104. It is to be appreciated that the terms hot and cold are intended to describe relative temperatures of the thermoelectric generator 100. Consequently, when the outer surface 102 of the air duct heats the hot side 106 of the thermoelectric generator 100 to a temperature greater than the cold side 108 an electric current is produced.

The thermoelectric generator 100 is cooled by natural convection, forced convection, or solid conduction. In the embodiment as shown in FIG. 6A, the thermoelectric generator 100 is cooled using natural convention. Specifically, outside air 110 (which is relatively cold) flows over the heat sink 104 of the thermoelectric generator 100. In the embodiment as shown in FIG. 6B, the thermoelectric generator 100 is cooled using forced convention. Specifically, the outside air 110 is channeled over the heat sink 104 of the thermoelectric generator 100 by a tube 112. In the embodiment as shown in FIG. 6C, the thermoelectric generator 100 is cooled using solid conduction. Specifically, a solid 114 having a high thermal conductivity is used to connect the cold side 108 of the thermoelectric generator 100 with the outside air 110. Some examples of solids having a high thermal conductivity include, but are not limited to, aluminum, graphene, and single wall carbon nanotubes. In another embodiment, the solid 114 is a heat pipe. A heat pipe is a two phase heat transfer device including an envelope, a working fluid, and a wick structure.

Turning now to FIG. 6D, in another embodiment the air duct 40 does not include the ultraviolet light source 30 (FIG. 7), the visible light source 48 (FIG. 2), or the emitter 84 (FIG. 4). Instead, the air duct 40 transmits the conditioned air 36. However, the outer surface 102 is still heated to a temperature that is greater than the outside air 110. Thus, a temperature differential still exists between the hot side 106 and the cold side 108 of the thermoelectric generator 100 sufficient to generate electric current.

Figure 7:
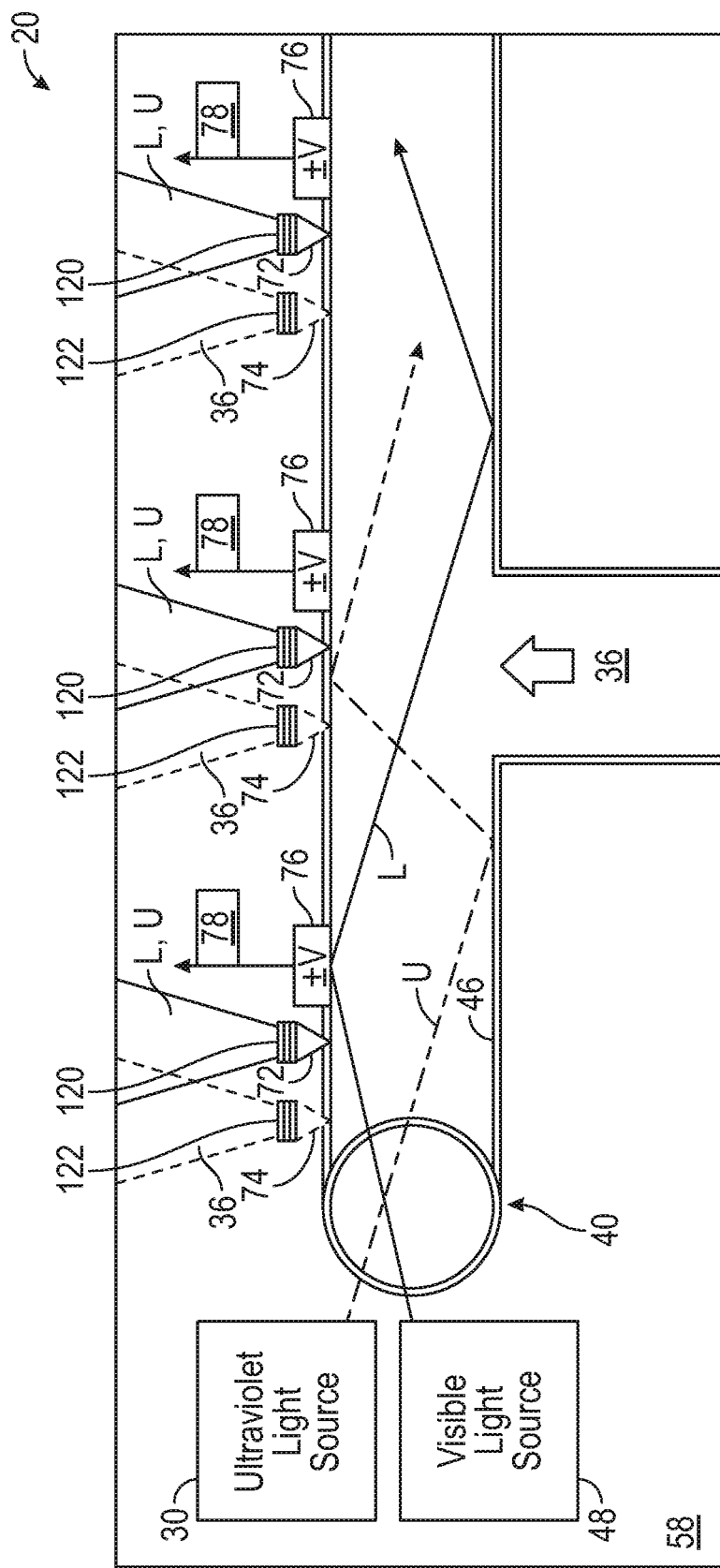
FIG. 7 is another embodiment of the air duct system shown in FIG. 2 further including an ultraviolet light source, according to an exemplary embodiment.

FIG. 7 illustrates yet another embodiment of the air duct 40 including the ultraviolet light source 30 configured to generate the ultraviolet light U. The source of ultraviolet light source 30 may be, for example, an ultraviolet laser or a low-pressure ultraviolet lamp. The ultraviolet light source 30 directs the ultraviolet light U along the reflective inner surface 46 of the air duct 40, where the ultraviolet light U sanitizes the conditioned air 36 flowing through the overhead air duct 22 is sanitized. In other words, the ultraviolet light U kills airborne germs, bacteria, and other contaminates that are suspended within the conditioned air 36 that flows through the air duct 40. The ultraviolet light U includes a germicidal wavelength ranging from 185 to 400 nanometers (nm). The germicidal wavelength range includes near ultraviolet wavelengths of about 220 nm to about 400 nm and far ultraviolet wavelengths of about 190 nm to about 220 nm. The power of the ultraviolet light source 30 may vary based on the size of the air duct 40, airflow rate, and the power of the ultraviolet light source 30, and in one embodiment may range from 100 Watts to 1 Kilowatt.

Continuing to refer to FIG. 7, the air duct system 20 further includes a plurality of ultraviolet optical filters 120 placed over each of the plurality of lighting apertures 72. The ultraviolet optical filters 120 allows for the visible light L to enter the interior cabin 58 and at the same time filters the ultraviolet light U. This is to prevent ultraviolet light expose to the passengers located in the interior cabin 58 of the aircraft 10. The air duct system 20 also includes a plurality of ultraviolet optical filters 122 placed over each of the plurality of air valves 74 as well. The ultraviolet optical filters 122 are configured to allows for the conditioned air 36 to flow to the interior cabin 58. In an embodiment, the ultraviolet optical filters 120, 122 are constructed of a glass that is opaque to wavelengths in the germicidal wavelength.

Figure 8:
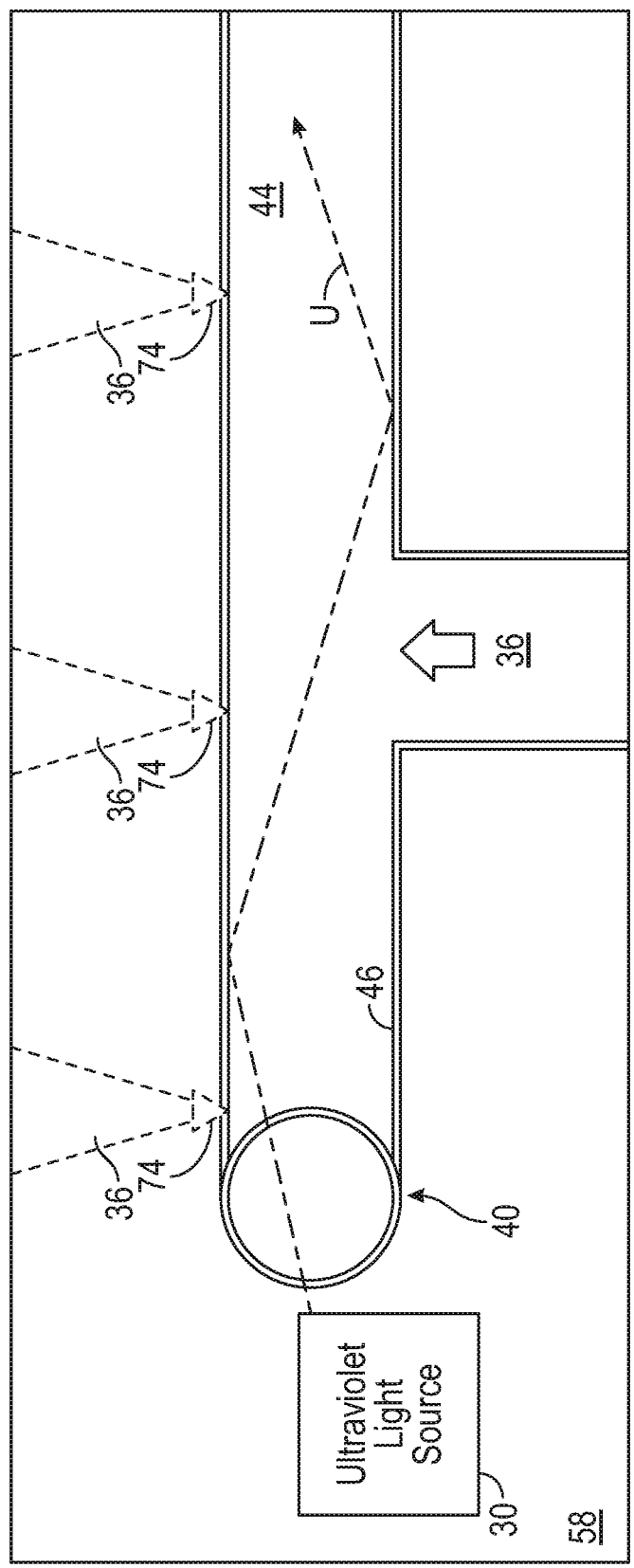
FIG. 8 is a schematic diagram of another embodiment of the air duct system including only the ultraviolet light source, according to an exemplary embodiment.

Although FIG. 7 illustrates both the ultraviolet light source 30 and the visible light source 48, in another embodiment the ultraviolet light source 30 is used alone. Referring now to FIG. 8, the air duct system 20 includes only the ultraviolet light source 30 to sanitize the conditioned air 36. Since the air duct system 20 in FIG. 8 does not transmit visible light, the inner reflective surface 46 does not require a relatively high reflectance that is described above (i.e., a reflectance of ninety-nine percent). Instead, the inner reflective surface 46 of the main body 42 of the air duct 40 includes a reflectance of at least twenty-five percent.

Figure 9:
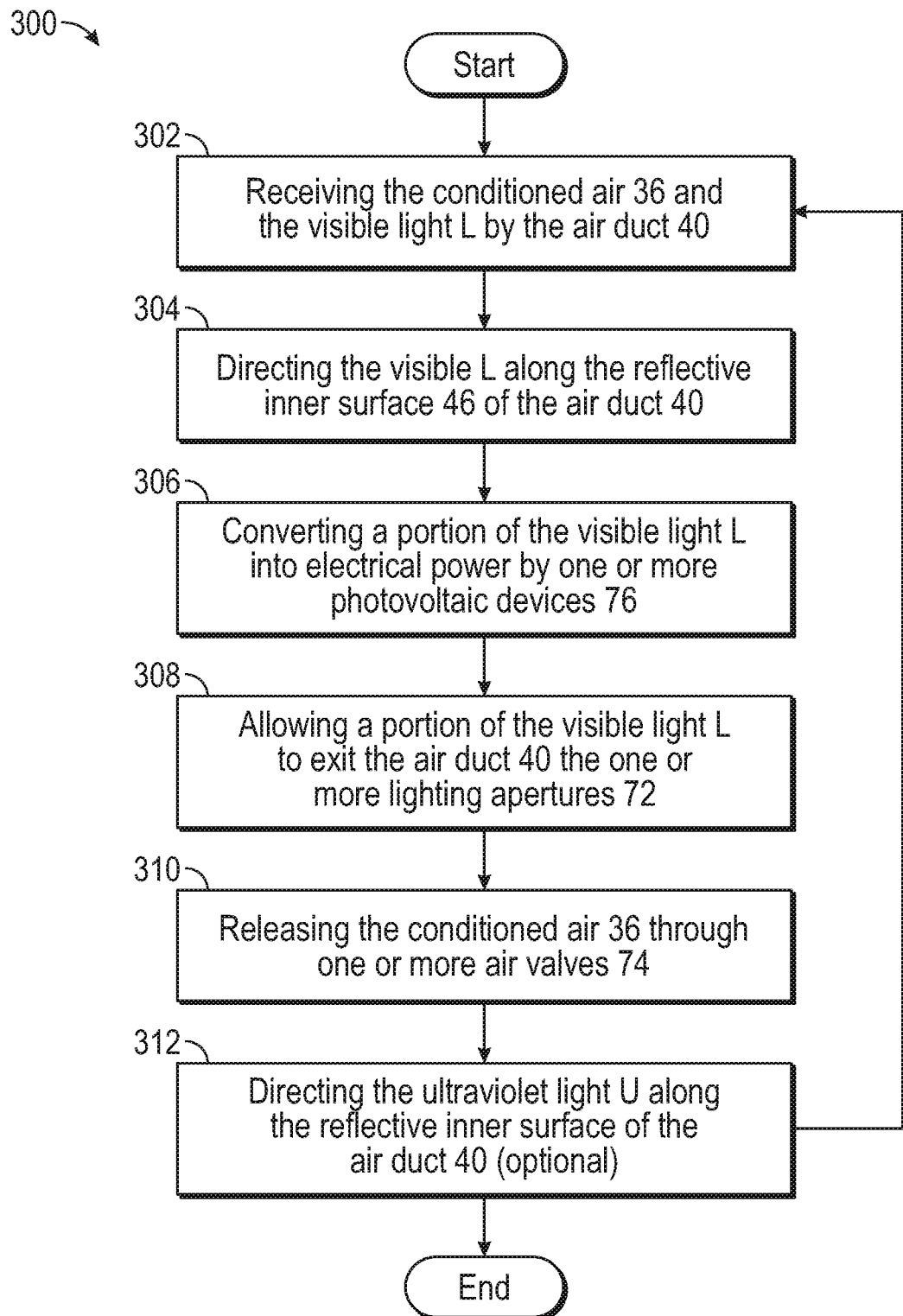
FIG. 9 is a process flow diagram illustrating a method for transmitting air, visible light, and electrical power by the disclosed air duct, according to an exemplary embodiment.

FIG. 9 is an exemplary process flow diagram illustrating a method 300 transmitting air, visible light, and electrical power through the air duct 40 of the aircraft 10. Referring to FIGS. 1, 2, and 9, the method 300 begins at block 302. In block 302, the air duct 40 receives the conditioned air 36 and visible light L. As mentioned above, the visible light L is generated by the visible light source 48. The method 300 may then proceed to block 304.

In block 304, the visible light L is directed along the reflective inner surface 46 of the air duct 40, where the visible light L reflects off of the reflective inner surface 46 and travels along the passageway 44 of the air duct 40. The method 300 may then proceed to block 306.

In block 306, a portion of the visible light L is converted into electrical power by one or more photovoltaic devices 76 disposed along the reflective inner surface 46 of the air duct 40. As mentioned above, the photovoltaic device 76 provides electrical power to a corresponding electronic device 78. The method 300 may then proceed to block 308.

In block 308, a portion of the visible light L is allowed to exit the air duct 40 through one or more lighting apertures 72 disposed along the main body 42 of the air duct 40. The method 300 may then proceed to block 310.

In block 310, the conditioned air 36 is released by one or more air valves 74 disposed along the main body 42 of the air duct 40. The method 300 may then proceed to block 312.

It is to be appreciated that block 312 is optional and may be omitted in some instances. In block 312, the ultraviolet light U (seen in FIG. 7) is directed along the reflective inner surface 46 of the air duct 40. As mentioned above, the ultraviolet light U includes a germicidal wavelength ranging from 185 to 400 nanometers. The method 300 may then terminate or, alternatively, proceed back to block 302.

Referring to FIGS. 1-7 and 9, the disclosed air duct system is configured to provide conditioned air, visible light, and electrical power. The electrical power is transmitted through the air duct in the form of visible light and is transformed into electrical power by photovoltaic devices. As a result, there is no wiring or cables to transmit electrical power to the overhead lights in an aircraft. Moreover, the photovoltaic devices provide electrical power to other electronic devices, such as individual television screens for each passenger. Accordingly, there is no wiring or cables included for transmitting electrical power to various electronic devices in the aircraft. This results in a significant weight savings, which in turn enhances fuel efficiency.

Figure 10:
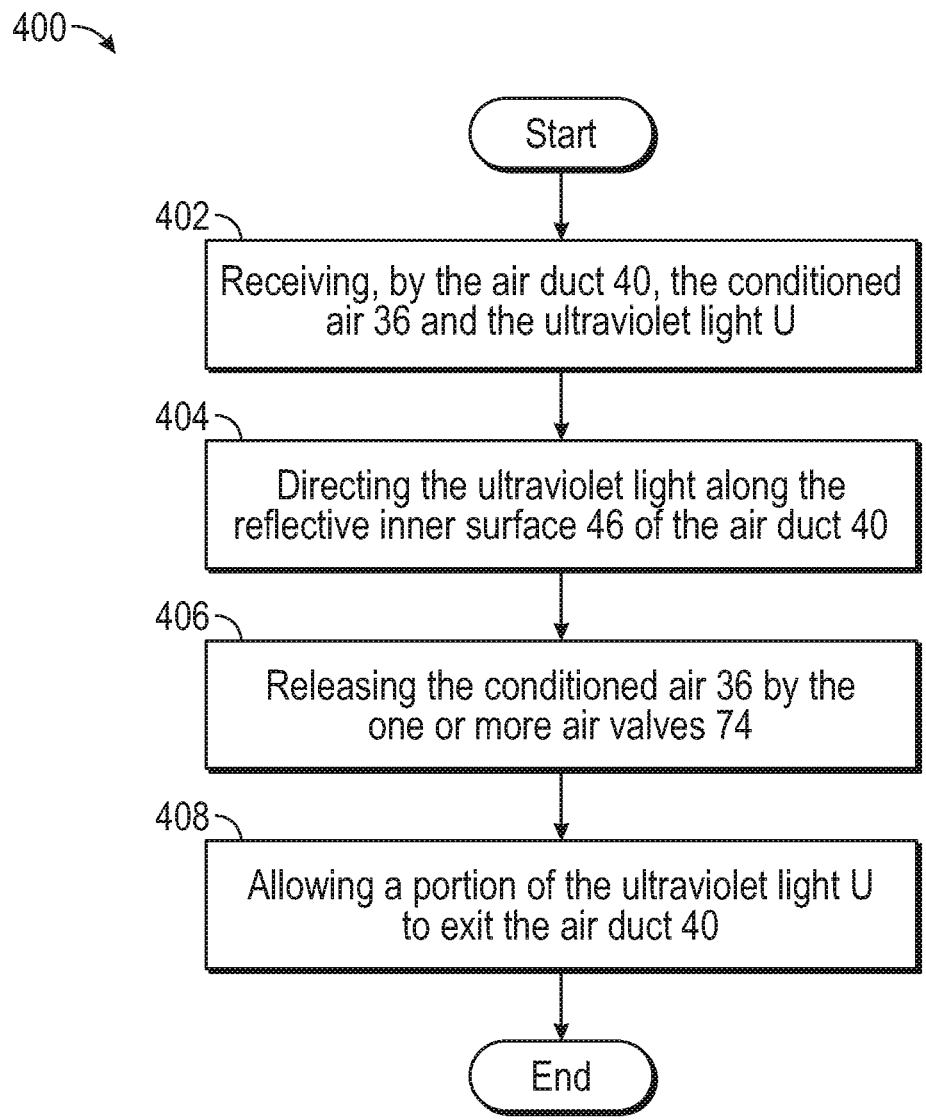
FIG. 10 is a process flow diagram illustrating a method for sanitizing air flowing through the disclosed air duct, according to an exemplary embodiment.

As mentioned above, in the embodiment as shown in FIG. 8, the ultraviolet light source 30 is used alone (i.e., without the visible light source 48). Turning now to FIG. 10, a process flow diagram illustrating a method 400 for sanitizing the conditioned air 36 in an aircraft 10. Referring now to FIGS. 8 and 10, the method 400 begins at block 402. In block 402, the air duct 40 receives the conditioned air 36 and ultraviolet light U. As mentioned above, the visible light L is generated by the ultraviolet light source 30. The method 300 may then proceed to block 404.

In block 404, the ultraviolet light U is directed along the reflective inner surface 46 of the air duct 40, where the ultraviolet light U reflects off of the reflective inner surface 46 and travels along the passageway 44 of the air duct 40, and sanitizes the conditioned air 36 flowing through the air duct 40. The method 300 may then proceed to block 406.

In block 406, the conditioned air 36 is released by one or more air valves 74 disposed along the main body 42 of the air duct 40. As mentioned above, the ultraviolet optical filters 122 is placed over the air valves 74 to prevent the transmission of the ultraviolet light U. The method 400 may then proceed to block 408.

In block 408, a portion of the ultraviolet light U is allowed to exit the air duct 40 through one or more lighting apertures 72 disposed along the main body 42 of the air duct 40. As mentioned above, a plurality of ultraviolet optical filters 120 are placed over the lighting apertures 72 to prevent the ultraviolet light U from traveling into the interior cabin 58 of the aircraft 10. The method 400 may then proceed terminate or proceed back to block 402.

Referring to FIGS. 8 and 10, the disclosed air duct system provides a lightweight approach for sanitizing the conditioned air throughout the interior cabin of an aircraft. This in turn prevents the transmission of infectious diseases that may occur among air travelers. In an embodiment, the ultraviolet light may kill some types of serious infectious diseases as well.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. An air duct system, comprising:
   an air duct having a main body, wherein the main body of the air duct defines a passageway having a reflective inner surface;
   a visible light source configured to generate visible light, wherein the visible light source directs the visible light along the reflective inner surface of the air duct; and
   one or more photovoltaic devices disposed along the reflective inner surface of the air duct, wherein a portion of the visible light generated by the visible light source is converted into electrical power by the one or more photovoltaic devices.

2. The air duct system of claim 1, further comprising one or more lighting apertures disposed along the main body of the air duct, wherein a portion of the visible light generated by the visible light source exits the air duct through the one or more lighting apertures.

3. The air duct system of claim 2, further comprising an ultraviolet light source configured to generate ultraviolet light, wherein the ultraviolet light source directs the ultraviolet light along the reflective inner surface of the air duct.

4. The air duct system of claim 3, further comprising one or more ultraviolet optical filters, wherein an ultraviolet optical filter is placed over each of the one or more lighting apertures.

5. The air duct system of claim 4, wherein the ultraviolet light includes a germicidal wavelength ranging from 185 to 400 nanometers.

6. The air duct system of claim 1, further comprising one or more air valves disposed along the main body of the air duct.

7. The air duct system of claim 1, wherein the visible light source comprises an array of light-emitting diodes (LEDs).

8. The air duct system of claim 1, wherein the visible light emitted from the visible light source has an angle of divergence of ten degrees or less.

9. The air duct system of claim 1, wherein the reflective inner surface of the main body of the air duct includes a reflectance of at least fifty percent.

10. The air duct system of claim 1, wherein the reflective inner surface of the main body of the air duct includes a reflectance of at least ninety-nine percent.

11. The air duct system of claim 1, further comprising a thermoelectric generator having a hot side and a cold side, wherein the hot side of the thermoelectric generator is positioned along an outer surface of the air duct.

12. The air duct system of claim 11, wherein the thermoelectric generator is cooled by natural convection, forced convection, or solid conduction.

13. A method for transmitting air, visible light, and electrical power through an air duct of an aircraft, the method comprising:
    receiving, by the air duct, conditioned air, and visible light;
    directing the visible light along a reflective inner surface of the air duct, wherein the visible light reflects off of the reflective inner surface and travels along a passageway of the air duct; and
    converting a portion of the visible light into electrical power by one or more photovoltaic devices disposed along the reflective inner surface of the air duct.

14. The method of claim 13, further comprising:
    allowing a portion of the visible light to exit the air duct through one or more lighting apertures disposed along a main body of the air duct.

15. The method of claim 13, further comprising:
    releasing the conditioned air by one or more air valves disposed along a main body of the air duct.

16. The method of claim 13, further comprising:
    directing ultraviolet light along the reflective inner surface of the air duct.

17. The method of claim 16, wherein the ultraviolet light includes a germicidal wavelength ranging from 185 to 400 nanometers.

18. The method of claim 13, wherein the visible light emitted from the visible light source has an angle of divergence of ten degrees or less.

19. The method of claim 13, wherein the reflective inner surface of the air duct includes a reflectance of at least fifty percent.

20. The method of claim 13, wherein the reflective inner surface of the air duct includes a reflectance of at least ninety-nine percent.

21. The method of claim 13, wherein the air duct further comprises one or more air valves disposed along a main body of the air duct.

* * * * *